United States Patent
Crews et al.

(10) Patent No.: US 6,632,676 B1
(45) Date of Patent: Oct. 14, 2003

(54) MULTI-PURPOSE REAGENT SYSTEM AND METHOD FOR ENUMERATION OF RED BLOOD CELLS, WHITE BLOOD CELLS AND THROMBOCYTES AND DIFFERENTIAL DETERMINATION OF WHITE BLOOD CELLS

(75) Inventors: Harold Richardson Crews, Coral Springs, FL (US); James Harrison Carter, II, Plantation, FL (US); Ted Sena, Naples, FL (US)

(73) Assignee: Clinical Diagnostic Solutions, Plantation, FL (US)

( * ) Notice: Subject to any disclaimer, the term of this patent is extended or adjusted under 35 U.S.C. 154(b) by 0 days.

(21) Appl. No.: 09/405,547

(22) Filed: Sep. 24, 1999

(51) Int. Cl.⁷ ............................................... G01N 31/00
(52) U.S. Cl. ............................... 436/18; 436/8; 436/10; 436/15; 436/17; 436/63; 436/164; 436/166; 436/174; 436/176; 436/179; 435/2; 435/40.5
(58) Field of Search ............................ 436/8–16, 17–19, 436/28, 39, 63, 74, 164, 166, 174, 176, 179, 546, 548; 435/2, 3, 7.24, 7.25, 15, 18, 28, 40.51, 962, 4

(56) References Cited

U.S. PATENT DOCUMENTS

| | | | | |
|---|---|---|---|---|
| 4,506,018 A | * | 3/1985 | North, Jr. | 436/10 |
| 4,704,364 A | * | 11/1987 | Carver et al. | 436/10 |
| 4,745,071 A | * | 5/1988 | Lapicola et al. | 436/63 |
| 5,227,304 A | * | 7/1993 | Wong | 436/17 |
| 5,380,664 A | * | 1/1995 | Carver et al. | 436/10 |
| 5,639,630 A | * | 6/1997 | Malin et al. | 435/28 |
| 5,882,934 A | * | 3/1999 | Li et al. | 436/66 |
| 5,888,752 A | * | 3/1999 | Malin et al. | 435/7.24 |
| 5,935,857 A | * | 8/1999 | Riesgo et al. | 436/18 |

* cited by examiner

Primary Examiner—Long V. Le
Assistant Examiner—Gailene R. Gabel
(74) Attorney, Agent, or Firm—Martin Fleit; Paul D. Bianco; Fleit Kain Gibbons Gutman & Bongini P.L.

(57) ABSTRACT

A novel reagent system for use with automated and semi-automated hematology analyzers including an essentially isotonic blood diluting reagent, a blood cell lysing and hemoglobin conversion reagent, and a second lysing reagent for differentiating white blood cells into classes by size and functional characteristics. The diluent reagent enhances properties for counting and sizing blood specimens, while stabilizing cellular volume and cellular integrity for many hours. The blood cell lysing reagent removes red blood cells and enables subsequent enumeration of white blood cells and simultaneous determination of hemoglobin without use of the toxic cyanide anion. The third lysing reagent and a companion quenching differentiates blood cells into classes by size and functional characteristics, based on d.c. impedance volume, conductivity/opacity and light scatter measurements. The companion quenching reagent adjusts pH and conductivity of the final measurement solution to match the analyzer system requirements. Novel methods for use of the reagents with automated and semi-automated hematology analyzers are also provided.

3 Claims, 3 Drawing Sheets

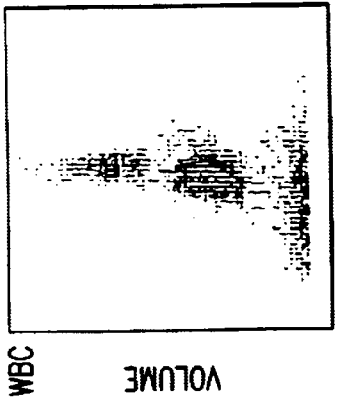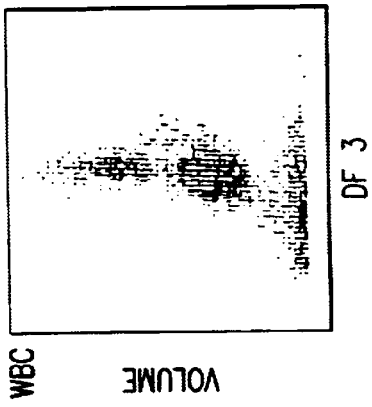
FIG. 2B — CDS-5 PD REAGENT SET D.C. VOLUME VS. OPACITY DF 3
FIG. 3B — COULTER SCATTERPAK REAGENT D.C. VOLUME VS. OPACITY DF 3
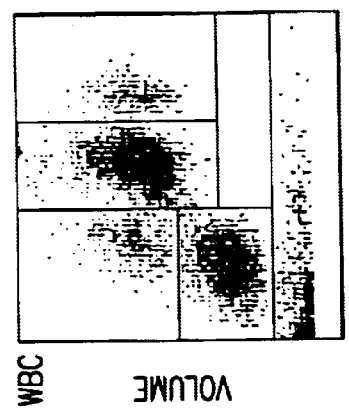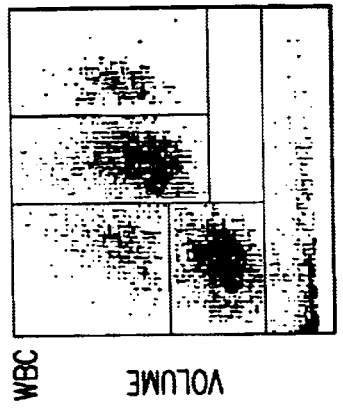
FIG. 2A — CDS-5 PD REAGENT SET D.C. VOLUME VS. LIGHT SCATTER DF 1
FIG. 3A — COULTER SCATTERPAK REAGENT D.C. VOLUME VS. LIGHT SCATTER DF 1

DF 1
1-BUTANESULFONIC ACID, SODIUM LYSE
D.C. VOLUME VS. LIGHT SCATTER

DF 3
1-BUTANESULFONIC ACID, SODIUM LYSE
D.C. VOLUME VS. OPACITY

DF 1
GLUTARIC ACID + HYDROCHLORIC ACID LYSE
D.C. VOLUME VS. LIGHT SCATTER

DF 3
GLUTARIC ACID + HYDROCHLORIC ACID LYSE
D.C. VOLUME VS. OPACITY

MULTI-PURPOSE REAGENT SYSTEM AND METHOD FOR ENUMERATION OF RED BLOOD CELLS, WHITE BLOOD CELLS AND THROMBOCYTES AND DIFFERENTIAL DETERMINATION OF WHITE BLOOD CELLS

BACKGROUND OF THE INVENTION

1. Field of the Invention

The invention relates to a multi-purpose reagent system and method for enumeration of red blood cells, white blood cells and thrombocytes and differential determination of white blood cells.

2. Description of the Prior Art

The art recognizes that the ability to resolve the various populations of blood cells into their constituent classes, particularly those of the leukocytes, provides an invaluable diagnostic aid in the study, diagnosis and treatment of various diseases. As is further appreciated, the greater the number of sub-populations that are identifiable and enumeratable, the more accurate and reliable the identification of any single sub-population is likely to be.

Previous scientific publications and patents have described reagents and methods for enumerating these cell types by a variety of mechanisms. U.S. Pat. No. 4,485,175 (to Ledis, et al.) describes a reagent system comprising a multipurpose blood diluent and a lysing reagent, and a method for utilizing same to produce a hemoglobin measurement and differentiation of white blood cells into at least one and up to three sub-populations of leukocytes. U.S. Pat. No. 5,731,206 (to Ledis, et al.) describes a lytic reagent composition, a kit of a lytic reagent system and a method for isolating, identifying and analysis of at least one and up to five sub-populations of leukocytes from a whole blood sample. Other representative patent references pertinent to this field include U.S. Pat. Nos. 3,874,852; 4,286,963; 4,346,018; 4,528,274 and 4,751,179. All are hereby incorporated by reference in their entirety.

SUMMARY OF THE INVENTION

This invention concerns certain novel compositions of matter (reagents) and novel methods of use of a set of reagents designed and matched for electronic enumeration and sizing of blood cells, utilizing automated and semi-automated hematology analyzers for the multiple purposes of counting and sizing red blood cells; counting, sizing and differentiating white blood cells according to their subtype; counting and sizing platelets in whole blood; and the photometric measurement of hemoglobin concentration. Effective measurement of the formed elements of a whole blood sample requires multiple steps, including counting and sizing of the red blood cells and platelets, followed by addition of a red blood cell hemolyzing reagent, thus permitting the enumeration and sizing of the remaining white blood cells.

Use of the present invention enhances the ability to resolve the various populations of blood cells into their constituent classes, particularly those of the leukocytes, and provides an invaluable diagnostic aid in the study, diagnosis and treatment of various diseases. As may be further appreciated, the greater the number of sub-populations that are identifiable and enumeratable, the more accurate and reliable the identification of any single sub-population is likely to be.

The diluent reagent of the present invention comprises an aqueous solution of chemical salts providing an electrically conductive solution to which a blood sample can be added to dilute the red blood cells, white blood cells and platelets to enable electronic counting, sizing and evaluation by d.c. impedance, rf conductivity or opacity (a normalization of the rf signal divided by the d.c. signal) and/or light scatter at one or more angles to the incident light beam. In order to separate the complex electrical signals emanating from such a dilute mixture, a first red blood cell lysing reagent is added to rupture (stromatolyse) the red blood cells and dissolve their membrane particles (stroma), such that the red blood cells no longer register in any of the measurements made by the analyzer system. The resulting solution may be counted, sized and evaluated by electronic and mathematical means to produce a volumetric representation of the remaining white blood cells into at least one size population up to three or more size populations. Simultaneously, the lysing reagent also reacts with the hemoglobin liberated from the lysed red blood cells, converts it chemically to a stable oxyhemoglobin derivative, which is then measured photometrically, and a hemoglobin concentration is calculated from a previous known hemoglobin concentration used as a standard.

In a second part of the invention, a lysing reagent is reacted with a blood sample, similarly destroying the red blood cells under acidic conditions of low osmolality and conductivity with an acid active natural detergent present, and resulting in the differentiation of white blood cells (leukocytes) into at least one and up to five component subtypes, specifically described by their morphology and function as lymphocytes, monocytes, granulocytes, eosinophils and basophils. Addition of a third reagent, called a quenching reagent, is required in order to adjust the pH to approximately neutral (i.e., 6.5 to 7.5) and to adjust the conductivity to about 18 to 20 milliSiemens per kilogram, as is usual for isotonically diluted blood specimens. Simultaneous measurement of parameters, such as volume, conductance or opacity, and light scattering ability have been used to differentiate white blood cell subtypes into at least one and up to five different categories. While functional tests of white blood cell subtypes are usually difficult to perform in automated analyzers, these electronic and optical parameters have been related to cellular function by scientific studies designed to correlate cellular function with cell volume, opacity and/or light scatter signals.

Although previous attempts to accomplish the foregoing have permitted performance of similar cellular enumerations and differentiations more or less accurately, nevertheless, the presence of hematological abnormalities and/or aging of the blood specimen post-phlebotomy which cause changes in the cellular response to chemical and electrical stimuli as provided by the analyzer system, have precluded prior compositions and methods from achieving the results of the present invention. These changed cellular responses usually result in changes in the chemical response, and subsequently, the appearance of the histogram and scattergram patterns of the cells. The subtypes are subsequently distorted from the usual presentation of fresh blood cells within the analyzer's output. This shifting or changing of the cellular response to measurement results in inaccuracies and possible misclassifications that may have medical consequences. These shifts also may cause error flags to be generated by the analyzer system that may further distort the true analytical picture. Additionally, the presence of such error flags requires the laboratorian to re-analyze the specimen by alternative means in order to provide a reliable result to the physician. Such is not the result, however, in the performance of the present invention.

The present invention overcomes and solves these problems encountered in the prior art by treating the abnormal and older, more fragile blood cells in a chemically more gentle manner, from which they can be measured and analyzed closer to their native, whole-blood state. Hematological analysis with better accuracy and fewer error flags is much more desirable in the medical laboratory. Thus, the clinician may receive more useful diagnostic information, eliminating the potential for erroneous data.

The task of improving the reagent designs and the analyzer system performance is made more difficult by the design of current hematology analyzer systems, which usually have fixed counting and sizing thresholds, fixed mathematical treatments (algorithms) of the measured data, and therefore, do not allow much leeway in the reagent chemistry for changes in cellular volumetric size and variant responses to the instrument algorithms. Changes in the analyzer's positioning of various cell subtypes due to cellular abnormalities and sample-age related changes in chemical behavior generally have resulted in misidentification or misclassification by the analyzer system in the past. By the use of the present invention and the application of a gentler, more cell-friendly chemistry within the analyzer system, cell positioning and electrical response changes can be reduced, thus, presenting a cell count and distribution more nearly like that of fresh blood specimens.

Several different models of electronic blood cell counting and sizing apparatus are useful in practicing the art of blood cell analysis, including Beckman Coulter Models MD, MD II, T Series analyzers (T540, T660, T890, ST, JT 1, JT 2 and JT 3), S Plus 4, 5 and 6, STKR, STKS, MAX-M and Gen•S; and other representative analyzers, such as Abbott Laboratories' CD3000, CD3500 and others; and TOA (Sysmex) Model 1600 and others.

It is an object of this invention to improve and remedy the many known deficiencies of hematology analysis systems, as discussed above, and additionally to simplify the reagents, remove any toxic components, remove any components that destabilize the hematology analysis system and to increase the stability of the hematology analysis system measurements, while reducing the sensitivity of the analyzer system to the effects of sample age and physiological abnormalities of the patient.

It is an additional object of this invention to provide a stable blood diluent environment for the analysis red blood cells and platelets, both from fresh patient samples and those that have aged since sample collection.

It is a further object of this invention to provide a reagent for a chemical reaction with a whole blood sample, whether freshly collected or aged since collection, that may permit the enumeration of the total number of white blood cells present, the differentiation of at least one and up to three sub-populations of leukocytes, and simultaneously provide a stable hemoglobin chromagen for determination of the hemoglobin concentration by photometric measurement, without requiring the use of toxic compounds such as cyanide to form said stable chromagen.

It is a still further object of this invention to provide an additional reagent system that can further subdivide leukocyte sub-populations of freshly collected or aged blood specimens into at least one and up to five distinct classifications for use in differential determination of the relative number of such cells in each sub-population by providing a means to lyse the red blood cells, then to stabilize the residual white blood cell mixture by addition of a quenching reagent for subsequent analysis.

It is yet another additional object of this invention to provide a novel reagent system for effective use in separating and differentiating white blood cell subpopulations, whether freshly collected or aged since collection, for the purpose of measurement by purely physical, electrical and light scattering means, and by immunological and immunochemical means by use of additional reagents comprising antibodies or antisera specific for one or more marker molecules on the surface or within the cellular contents of said sub-populations.

It is a further object of this invention to provide a method for the performance of these analyses, including: a) the counting and sizing of red blood cells and platelets from a fresh or aged blood sample, b) the removal of red blood cells and the subsequent measurement of at least one up to three sub-populations of white blood cells from freshly collected or aged blood samples, c) the conversion of the liberated hemoglobin to a stable derivative for photometric measurement, d) the differential determination of at least one and up to five sub-populations of leukocytes from freshly collected or aged blood samples by measurement of physical, electrical and light scatter properties, and e) measurement of the immunochemical or immunological response of any such sub-populations to antibodies or antiserum specific for one or more marker molecules on the surface or within the cellular contents of said sub-populations.

Other and further objects and advantages of the present invention will become more apparent from the detailed description of the preferred embodiments as set forth in the following when taken together with the drawings.

BRIEF DESCRIPTION OF THE DRAWINGS

FIG. 2A is a scattergram of Example II, volume v. light scatter, using a 5 part differential lysing reagent.

FIG. 2B is a scattergram of Example II, volume v. opacity scatter, using a 5 part differential lysing reagent.

FIG. 3A is a scattergram like FIG. 2A using known reagents.

FIG. 3B is a scattergram like FIG. 2B using known reagents.

DETAILED DESCRIPTION OF PREFERRED EMBODIMENTS OF THE INVENTION

Figure 1:
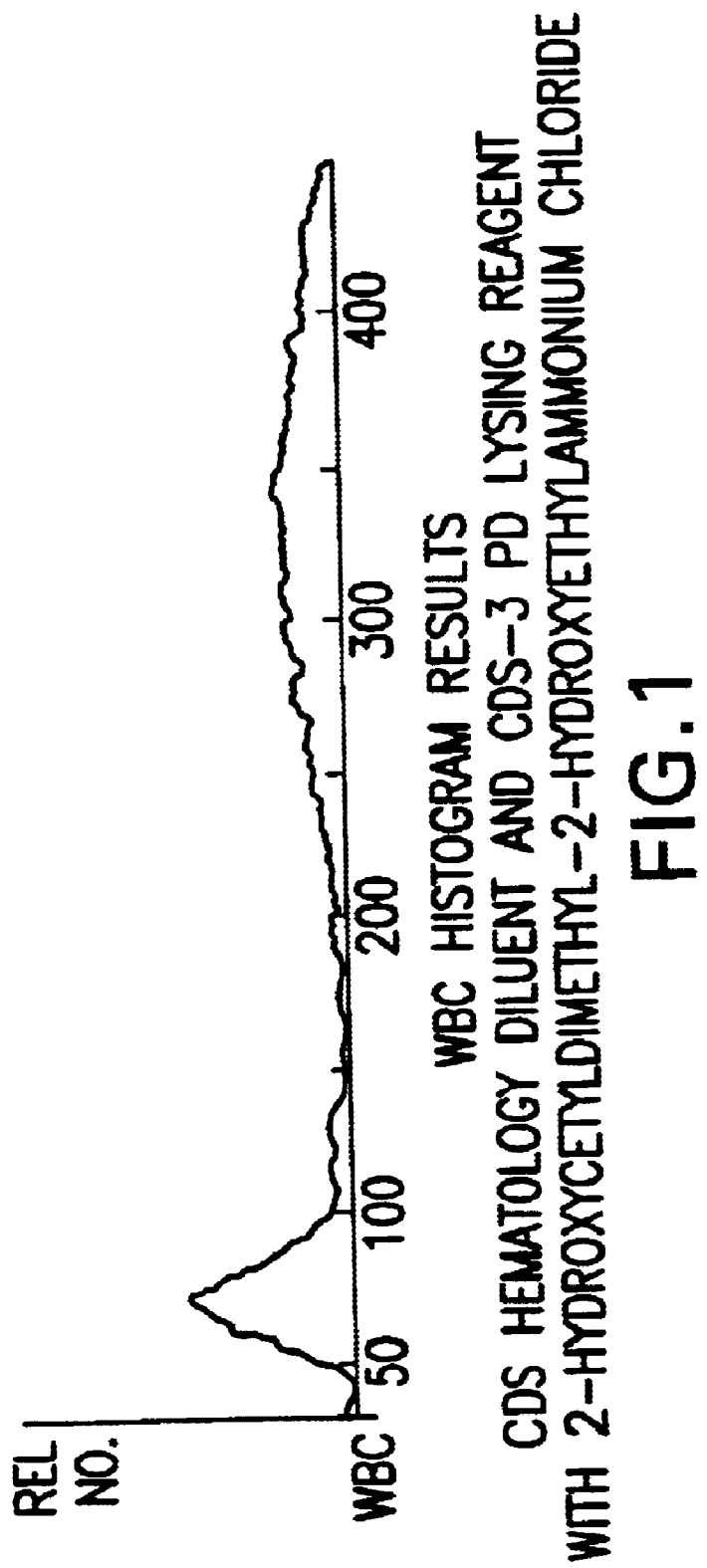
FIG. 1 is a WBC histogram of Example I.

The present invention concerns compositions of matter and methods used to obtain medical diagnostic information from a whole blood specimen utilizing techniques and measurement parameters built into existing commercial hematology analyzer systems. Specifically, a 1.6 $\mu$L volumetrically measured sample of whole blood specimen is precisely diluted and suspended in 10 mL (1:6,259 dilution) of a hematology diluent reagent is prepared for the red blood cell and platelet count. This reagent is designed to maintain blood cell sizes, shapes and chemical reaction responses near to the native state of said blood cells in whole blood for at least the period of time required for analysis, about one to about three minutes. After this appropriate dilution, the analyzer can count and size the red blood cell and thrombocyte populations of the whole blood sample, and store the results in an electronic memory within the analyzer system in a more advantageous manner.

In a further processing, one part of the novel first dilution of the whole blood specimen is reacted with an amount of a novel red blood cell lysing reagent to simultaneously dissolve the red blood cell membranes without also destroying the white blood cells. Specifically, a 27 µL sample of additional whole blood specimen is diluted with an additional 6.0 mL (1:224 dilution) of hematology diluent reagent followed by the addition of 1.0 mL of strong lysing reagent for white blood cell counting and differentiation, and hemoglobin determination. This step simultaneously dissolves the red blood cell membranes without also destroying the white blood cells. The hemoglobin contained within each red blood cell is converted chemically into a stable hemoglobin complex for photometric analysis in an optical chamber of the hematology analyzer instrument, containing a light source, an optical path of constant and known length and a light detector. The remaining white blood cells in this dilution and suspension are counted and sized by d.c. impedance electronic aperture detection, resulting in total count of white blood cells and some information about the size distribution in a more advantageous manner. Certain sub-populations of white blood cells larger than a predetermined electronic size threshold, which includes only lyse-resistant red blood cell and white blood cell populations, may be enumerated and differentiated in this manner. This count is analyzed to report total cell counts and average cell sizes of the larger formed cells within a blood specimen, specifically nucleated red cells and white blood cells.

In certain hematology analyzer systems so equipped, such as Beckman Coulter Models STKS, MAX-M and Gen•S analyzer systems, a second group of measurement sensors and a flowcell detection chamber, often equipped with a laser or other highly focussed light source, is used to measure more accurate sub-populations of white blood cells from a separate blood specimen. Specifically, about 31 µL of volumetrically measured blood specimen is added to about 1,070 µL of a second, weak lytic reagent, which also destroys the red blood cells in a brief amount of time (about 10 seconds). This novel reagent removes the more numerous red blood cells, but permits the separate observation of the white blood cell components as a group of subpopulations based on their native volume, conductivity (opacity) and light scattering ability, which is correlated with their biological function.

About 196 µL of another novel reagent, called a quenching reagent is added. This novel quenching reagent is designed to rebalance the suspension pH to about 6.5 to about 7.5 and to simultaneously rebalance the conductivity and osmolality of the suspension to about 18.0 to 20.0 milliSiemens/cm and to about 250 to 350 milliosmole/kg, respectively. Measurements of d.c. impedance volume, light scattered by the cells within the sample suspension and electrical conductivity and a normalized parameter known as opacity (r.f. conductivity divided by d.c. impedance) are recorded. Based on this more advanced chemistry method and these physical and electronic sensors within the analyzer system, at least one to as many as five different subpopulations of white blood cells, based on the cellular structure and function, may be produced in a more advantageous manner. In this system, the subpopulations are separated and differentiated into white blood cell sub-types according to their volume, conductivity and light scatter signals. When combined mathematically with the total white blood cell count, as determined in the previous step, the analyzer is now capable of reporting a white blood cell differential count from one to as many as five different sub-types.

The above mentioned objects of the invention are achieved by the novel specifically improved individual reagent components that work together to improve system function beyond the current art. These novel and improved reagents will, in the various analyzer environments intended to utilize reagent components of these types, provide a stable dilution of red blood cells and platelets for counting and sizing, and white blood cell suspensions suitably stable to be selectively isolated, differentiated and identified into at least one and up to five sub-populations.

The diluent reagent is designed to suspend and dilute red blood cells, platelets and white blood cells in a manner suitable for individual cell counting and sizing, without causing significant changes in their respective sizes, shapes or internal constituents. This novel diluent reagent consists essentially of a single alkali metal salt, which dissociates into individual ions, establishing the majority of the isotonicity, osmolality and conductivity of the reagent. Representative alkali metal salts include sodium chloride, potassium chloride, sodium sulfate, potassium sulfate, sodium nitrate and potassium nitrate.

Buffering means, comprising complex carboxylic acids, such as, for example, 1,2-ethanedioic acid (oxalic acid); 1,3-propanedioic acid (malonic acid); cis-2-butenedioic acid (maleic acid); 1,3-butanedioic acid (succinic acid); 2,3-dihydroxy-1,4-butanedioic acid (tartaric acid); 2-hydroxyethane-2-carboxylic acid (lactic acid), 2-hydroxy-1,2,3-propane tricarboxylic acid (citric acid), 2,3,4,5,6-pentahydroxy-2,3-hexenecarboxylic acid-4-lactone (ascorbic acid) and other complex carboxylic acids, and the sodium salts thereof, serve to control the pH of the diluent reagent. Additionally, disodium ethylene dinitrilo-tetraacetic acid (EDTA) is incorporated to complex transition and heavy metals, such as iron and lead, which are frequently impurities in salt preparations, to prevent precipitation of complexes of these materials. Also included are various germicides and anti-bacteriostatic compounds to prevent the growth of microorganisms in the diluent reagent.

The salts influence the changes in size and shape of all of the cellular constituents of whole blood, especially the red blood cells and the lyse-treated white blood cells. Use of a single salt in the diluent reagent provides significantly better predictability of blood cell behavior after suspension and prior to counting and sizing. Control of the salt's concentration provides: a) consistent osmotic pressure on the cell membrane; b) consistent conductivity resulting in predictable signal responses of the cells to the direct currents (d.c.) and radio frequency/alternating currents (rf/a.c.) used for measurement; and c) consistent optical indices of refraction resulting in stable light scattering measurements. Use of a single salt represents an improvement over the multi-salt compositions of other, previous diluent reagents. Minor variations in the salt composition ratios, as well as, unidentified contaminating salt ions, lead to variations in cell response to the sensing systems in common usage in hematology analyzers. Rf/a.c. sensing is particularly sensitive to changes in ionic composition, due to changes in the solution conductivity, and corresponding changes in cellular conductivity. Opacity, a calculated parameter derived from normalizing the conductivity by dividing it by the d.c. volume, is used to locate and enumerate the basophil population by plotting its position in a different reference frame as a single, separated sub-population.

Whereas use of sulfate salts, such as sodium sulfate, as a constituent in a multi-component salt composition for a diluent reagent has been reported to benefit hematology analyzer systems by its ability to solubilize abnormal blood plasma proteins, especially immune globulins, thus preventing them from precipitating from solution, nevertheless, the use of only one sulfate is novel. Elevated WBC counts also have been reported to interfere with accurate hemoglobin measurements due to physical turbidity of the analysis solution by the elevated white blood cells, causing photometric measurements to be inaccurately biased to higher readings. Concentrations of sulfate in the diluent reagent solution greater than about 1% render these turbidity-causing cells more transparent in the photometric measurement, thus reducing that interference.

Preservatives can be added to these formulations to prevent the growth of microorganisms, yeasts and molds that would interfere with the ability of the analyzer system to count and size blood cells. These are traditional additives, comprising water-soluble compounds, such as methyl paraben, propyl paraben, and commercial antimicrobials, such as Proclin 150 and Proclin 300 (Supelco, Bellefonte, Pa.), Germall II (ISP Technologies, Chattam, N.J.) and Bronidox-L (Henkel, Emery Group, Cincinnati, Ohio) and other similar agents. The concentrations of such additives must be controlled to levels low enough to be compatible with the primary purpose of the functional components of the system, while retaining effectiveness against expected levels of microbial contamination.

A strong lytic reagent, capable of stromatolysing red blood cells and of reducing platelets to volumes below the threshold of detectability by the analyzer's counting and sizing measurement, produces a total white blood cell count and 3-part white blood cell differential. This reagent must be designed with a balance of lysing agent strengths to avoid reducing the volume of all white blood cell subtypes into one population at minimal terminal cell volume. Lymphocytes are the most sensitive to lysing reagents containing quaternary ammonium salts, while granulocytes are the least sensitive to these types of reagents. Monocytes, eosinophils and basophils are intermediate in sensitivity to these types of quaternary ammonium salt lysing reagents. Balancing various chain lengths of quaternary ammonium salt compounds to provide terminal volume lysis of lymphocytes, without appreciable cellular destruction, and with intermediate and low volume-shrinkage lysis of the other cellular subtypes, is a difficult process with many compromises between high and low lytic strength quaternary ammonium salts. Reagent that is too strong results in collapse of the cellular volume distribution to a restricted range of volumes, resulting in reduced ability to discern different cell subtypes. Reagent that is too weak will not adequately lyse all RBCs, which will contaminate or even obliterate the white cell distributions entirely. The commonly used trimethyl long-chain quaternary ammonium salts ($C_{12}$ or dodecyl, $C_{14}$ or tetradecyl and $C_{16}$ or hexadecyl) have lytic effects on all of the white cell subtypes, increasing in lytic strength with increasing carbon chain length, but decreasing in water (polar) solubility. These compounds all affect lymphocytes strongly, and the other subpopulations moderately to strongly, increasing in strength with carbon chain length. The dodecyl salt has the most moderate effect on monocytes, eosinophils and granulocytes of any of these three compounds. Use of a diluent reagent made predominantly of sodium sulfate and having a higher conductivity also contributes to protecting the monocytes, eosinophils and granulocytes, moderating the strong effects of quaternary ammonium salt reactivity.

The current invention combines the use of tetraalkylammonium halide salts, such as dodecyltrimethylammonium halide salts, tetradecyltrimethylammonium halide salts, dioctyldimethylammonium halide salts, didecyldimethylammonium halide salts and didodecyldimethylammonium halide salts, as the major lytic component. These compounds have relatively weaker lytic action on the non-lymphocyte components. In addition, another class of quaternary ammonium compounds with unexpectedly mild but thorough lysing action have been identified to moderate the cellular populations almost independently to provide a controllable histogram of white cell subtypes. Quaternary ammonium salt compounds with three shorter ($C_{8-12}$) carbon chains and one methyl group, such as trioctylmethylammonium halide salts, tridecylmethylammonium halide salts and tridodecylmethylammonium halide salts unexpectedly provide strong enough lytic action to contribute separation between the granulocyte population and the monocyte/eosinophil population without exerting lytic action that is too strong. Increasing the concentration of this material provides increasing separation up to a limiting concentration, and then all cell populations begin to collapse to lower volumes. Addition of yet a third quaternary ammonium salt compound having more polar (water-soluble) characteristics, such as 2-hydroxycetyl-2-hydroxyethyldimethylammonium halide salts, provides significant moderation to lytic strength, especially towards the granulocyte subtype, when mixed with alkyltrimethylammonium and dialkyldimethylammonium halide salts, together with trialkylmethylammonium halide salts. The hydroxyl groups are thought to render the material more polar in aqueous environments, and, therefore, less soluble in non-polar environments, such as the lipid components of the white blood cell membrane structure. Together with the effects of the sulfate ion from the diluent reagent, a white cell subtype histogram is provided that independently reduces the lytic effect on granulocyte subtypes, while maintaining minimum terminal volume shrinkage of the lymphocyte subtype cells. This results in an exceptional separation of white blood cell subtypes for differentiation and enumeration by the analytical system.

Hemoglobin concentrations deriving from the total hemoglobin content of the red blood cells is also sequentially measured in the lysis solution. After the white blood cell counting and sizing is complete, the remaining solution is subjected to photometric measurement in a standard optical cell, comprising a transparent fluid passage with an orthogonal light source, filtered to a narrow band of wavelengths, and an electronic light detector. Previously, hemoglobin measurements have been performed by reacting the lysing solution containing released hemoglobin with cyanide anion to cause formation of the very stable cyanohemoglobin derivative. With automatic hematology analysis apparatus, hemoglobin is generally measured at approximately the same time in the analysis cycle for every specimen. Thus, time control affords very stable results even when the hemoglobin derivative may not be considered stable for long periods of time.

In the present invention, lysis of the red blood cells yields a white blood cell suspension and a hemoglobin complex with the quaternary ammonium salts, which is then oxygenated by dissolved oxygen in the solution. This oxyhemoglobin complex is quite stable enough with respect to the time required by the analyzer's measurement cycle to be accurately measured by the hemoglobin photometer.

In hematology analyzer systems so equipped, a much more gentle lytic reagent is added separately to a second blood specimen to achieve stromatolysis of the red blood cells and platelets, while preserving the white blood cells in a near native state with respect to their original size (d.c. impedance volume), a.c. electrical conductivity and light scattering ability. Lysis action is accomplished by chemical interaction of hypo-osmotic solution conditions, controlled quantities of acid or acid-like compounds and a mild detergent. Lytic reagent solutions with osmolality less than 150 milliosmoles per kilogram are effective as hypo-osmotic lysing solutions. Several types of acid compounds have been found to be effective, especially carboxylic acids of more complex chemical structure than the unsubstituted $C_1$, to $C_3$ alkanoic acids. Particularly effective as acid sources are, for example, 2-chloro- and 2-fluoroacetic acids, 2-hydroxyacetic acid (glycolic acid), 2,3-dihydroxypropanoic acid (glyceric acid), 1,5-pentandioic acid (glutaric acid) and 2,3,4,5,6-pentahydroxyhexanoic acid (gluconic acid). Surprisingly, there are some inorganic mineral acid-forming compounds that are particularly effective as acid sources for this lytic reaction, including sodium pyrosulfate, sodium hydrogen sulfate (bisulfate), potassium pyrosulfate and potassium hydrogen sulfate (bisulfate). Additionally, there are some salts of alkylsulfonic acids that surprisingly yield effective results, such as 1-butanesulfonic acid sodium salt. This material is only slightly acidic in aqueous solution (pH about 5.0 to about 5.5), and yet it produces exceptionally debris-free white blood cell differentials, comprising at least one up to five subpopulations of white blood cell sub-types. Further additionally, a mixture of a weak organic acid, such as glutaric acid, together with a small amount of a mineral acid, such as hydrochloric acid, also surprisingly yield effective results, apparently due to the slow shifts in acid equilibrium, producing acid ions continuously but at relatively low concentrations.

A mild detergent material, such as the natural detergent "saponin", which is derived from the bark of quillaja trees, has been found to be effective is removing red blood cells and platelets, while sparing white blood cells from destruction. Use of saponin at appropriately low concentrations prevents the detergent from attacking the more robust white blood cells. The preferred concentration of saponin found effective in the present invention is from about 0.06% to about 0.15% when mixed with acid-forming reagents and in hypo-osmotic solution less than 150 milliosmoles per kilogram.

This lytic reagent may also contain other traditional additives, such as antimicrobial, antiyeast and antimold preservative compounds, such as methyl paraben, propyl paraben, Proclin 150 and Proclin 300 (Supelco, Bellefonte, Pa.), Germall II and Germaben (mixture of Germall II and methyl and propyl parabens) (ISP Technologies, Chattam, N.J.) and other effective preservative means. The concentrations of such additives must be controlled to levels low enough to be compatible with the primary purpose of the functional components of the system, while retaining effectiveness against expected levels of microbial contamination.

After a suitable reaction time, a second reagent, called a quenching reagent, is added to reduce the acidity by adjusting the pH to about 6.5 to about 7.5, and to moderate the hypo-osmotic condition by adding salt ions to adjust the osmolality of the solution to about 285 to about 350 milliosmoles/kg and to adjust the conductivity of the solution to about 18 to about 20 milliSiemens/cm. The preferred composition of this quenching reagent is comprised of a single, simple salt, such as sodium chloride, sodium sulfate, sodium carbonate, sodium bicarbonate and the potassium salts of these same anions. This salt provides the majority of anions and cations to readjust the osmolality of the lytic solution to a range compatible with the d.c. impedance and a.c. conductivity requirements of the analyzer. Additionally, this quenching reagent contains a buffering means, in effective amounts as required to adjust the pH to about 6.5 to about 7.5, as required by the white blood cells to remain stable. Many buffering compounds have been found to be effective, but N-(2-hydroxyethyl)piperazine-N'-ethanesulfonic acid (HEPES) and its sodium salt, members of the Good's family of organic buffers, has been found to be the most effective. This reagent stops the lysing actions and results in a suspension of white blood cells, which is then subjected to simultaneous measurement of d.c. impedance (cell volume), a.c. conductivity and opacity (conductivity divided by d.c. volume) and scattering angles of monochromatic light, measured at low angles to the incident light beam (0 to 25°) in a specially equipped flow cell. The data collected from these three sensors is mathematically processed and plotted in 3-axis space to give data clusters corresponding to the various sub-types of white blood cells, including, lymphocytes, monocytes, granulocytes, eosinophils and basophils.

The quenching reagent may also contain other traditional additives, such as antimicrobial, antiyeast and antimold preservative compounds, such as methyl paraben, propyl paraben, Proclin 150 and Proclin 300 (Supelco, Bellefonte, Pa.), Germall II and Germaben (mixture of Germall II and methyl and propyl parabens) (ISP Technologies, Chattam, N.J.) and other effective preservative means. The concentrations of such additives must be controlled to levels low enough to be compatible with the primary purpose of the functional components of the system, while retaining effectiveness against expected levels of microbial contamination.

The reagent system of this invention comprise aqueous solutions in amounts necessary to suspend and dilute blood cells for hematology analyzer counting and sizing, and for the differential lysis of red blood cells and platelets to produce white blood cell and hemoglobin suspensions suitable for hematology analysis. The diluent reagent of this invention is preferably described as a water-soluble mixture of a single alkali metal salt, a buffer and preservatives suitable to simultaneously produce an osmolality of about 285 to about 335 milliosmoles per kilogram, a conductivity of about 18 to about 20 milliSiemens per centimeter at 25° C. and a pH of about 7.0 to about 7.2. The preferred alkali metal salt is sodium chloride or sodium sulfate, and most preferably sodium sulfate. In its preferred embodiment, the sodium sulfate will range in concentration from 1.5 to 1.8%, and most preferably from 1.5 to 1.6%. The buffering means preferably comprises a balanced solution of citric acid and sodium citrate, such that the resulting pH of the entire solution is about 7.0 to about 7.2. In its preferred embodiment, the citric acid will range in concentration from about 0.1 to about 0.3%, and most preferably from about 0.18 to 0.20%, with sodium citrate, formed in situ from sodium hydroxide to produce a buffer salt couple with a final pH value preferably between 6.8 and 7.4, and most preferably between 7.0 and 7.2. The diluent reagent may optionally contain antimicrobial preservative compounds, as required to prevent the growth of microorganisms. It may contain preferably one or more of: a) about 0.001 to about 0.004%, and most preferably about 0.002 to about 0.003% of Bronidox-L (Henkel, Emery Group, Cincinnati, Ohio); b) preferably about 0.02 to about 0.07%, and most preferably about 0.04 to about 0.06% of Proclin 150 (Supelco, Bellefonte, Pa.); c) preferably about 0.01 to about 0.05%, and most preferably about 0.03 to about 0.04% of Proclin 300 (Supelco, Bellefonte, Pa.); and/or d) about 0.05 to about 0.4, and most preferably about 0.1 to about 0.25% of Germall II (ISP Technologies, Chattam, N.J.).

The strong stromatolysing reagent of this invention can be described as a water-soluble mixture of quaternary ammonium salt compounds, balanced for chemical lytic strength against whole blood cells to be strong enough to remove red blood cells and platelets, without destroying or significantly damaging the remaining white blood cells. A preferred embodiment of the strong lytic reagent comprises a solution of dodecyltrimethylammonium chloride, preferably from about 2.5 to 3.5% by weight, and most preferably from about 2.8 to about 3.0%. Additionally, the strong lytic reagent contains a short chain alkyl quaternary ammonium salt, comprising trioctylmethylammonium chloride (Adogen 464, Witco, Janesville, Wis.), preferably about 0.05 to about 0.15%, and most preferably from about 0.08 to about 0.12% by weight; and a third component, 2-hydroxycetyl-2-hydroxyethyldimethylammonium chloride (Dehyquart E, Henkel, Emery Group, Cincinnati, Ohio), preferably from about 0.05 to about 0.3% and most preferably from about 0.15 to about 0.25% by weight.

Example 1 shows one possible composition of the diluent reagent and the strong lytic reagent, and is illustrative of a composition of matter to practice this invention.

Example I

A hematology diluent reagent, as described above, was prepared from standard National Formulary, United States Pharmacopoeia or American Chemical Society grade chemicals, containing:

1.57% (w/v) sodium sulfate, anhydrous 0.19% (w/v) citric acid, anhydrous 0.13% (w/v) sodium hydroxide (approximate)

0.1% (w/v) disodium EDTA dihydrate 0.011% (w/v) procaine hydrochloride 0.0025% (w/v) Bronidox-L (Henkel, Emery Group, 5-bromo-5-nitro-1,3-dioxane)

0.05% (w/v) Proclin 150 (Supelco antimicrobial mixture)

0.2% (w/v) Germall II (ISP Technologies, diazolidinyl urea)

Diluted to 1 liter with deionized water and filtered through a 0.2 micron filter to remove small particulates.

The pH was about 7.0 to 7.2, the osmolality was about 295 to about 325 milliosmoles/kg and the conductivity was about 19.4 to about 19.7 milliSiemens/cm.

A three-part differential lysing reagent was prepared from standard, commercial grade quaternary ammonium salt compounds containing:

5.8% (w/v) dodecyltrimethylammonium chloride (Akzo Nobel, Arquad12-50)

0.1% (w/v) tri($C_8$–$C_{12}$)methyl ammonium chloride (Witco, Adogen 464)

0.2% (w/v) 2-hydroxycetyl-2-hydroxyethyldiemthylammonium chloride (Henkel, Emery Group Dehyquart E)

Diluted to 1 liter with deionized water and filtered through a 0.2 micron filter to remove small particulates.

A 28 µL sample of whole blood is mixed with 6 mL of hematology diluent reagent and 1 mL of the lysing reagent is added. After about 5 seconds of mixing, the solution is analyzed by a d.c. impedance signal through a 100 micron diameter aperture. The resulting electrical pulses are recorded and sorted into discrete electronic channels based on the integration area of each pulse. These processed data are plotted versus numbers of events to obtain a histogram, such as that shown in FIG. 1.

Mathematical algorithms within the analyzer instrument are utilized to separate these histogram curves into three discrete subpopulations of lymphocytes, monocytes/eosinophils and granulocytes. The sub-populations in FIG. 1 are spread well to the right-hand end of the histogram plot, while the margin of low counts between the left-hand "Y" axis and the counting threshold at channel 45 is enhanced. These factors provide the analyzer instrument with a greater degree of subpopulation separation, giving rise to a more accurate expression of the true differential distribution. In addition, the low count level at channel 45 also provides a much better total WBC count, since none of the smallest subpopulation of cells fall below the threshold at channel 45. Confluence of the data set at the right-hand end of the histogram to reach the baseline ensures that all white blood cells are detected in the histogram, resulting in accurate measurements of total white blood cell count, as well as inclusion of all cells in the histogram differential.

The current invention of a 5-part differential reagent set, comprising a moderate strength lytic reagent and a quenching reagent, has also provided enhanced advantages in separating white cell subpopulations to a greater degree and in a more definable manner than that of existing reagent technologies. Previous 5-part differential reagent sets (consisting of an hypotonic, acidic lysing agent, followed by a stabilizing or quenching reagent that functions to rebalance the pH and the salt concentration—and concurrently, the solution conductivity) acted as acid-enhanced, detergent-enhanced "hypotonic" lytic agents, inducing red cell membranes to become porous by the action of low tonicity and subsequent acid attack of any membrane channels that formed. After poration, the fluid contents of the cell leak out into the solution environment, while the membrane envelopes are reduced into small, non-interfering pieces. Removal of the red cell component without undue harm to the white cell component allows enumeration and sizing or other differentiation of this component. This lytic reagent comprises a weak, aqueous solution of a natural detergent called saponin and a low concentration of an acid-forming compound, such as a substituted short chain aliphatic acid, a complex organic carboxylic acid, a mineral acid half salt or an alkyl sulfonic acid sodium salt.

This reagent is characterized by a low osmolality (usually 100 milliosmoles/kg or less) compared to an isotonic solution of 285 milliosmoles/kg or more. The lytic reagent comprises an aqueous solution of potassium pyrosulfate, preferably at a concentration from about 0.02 to about 0.06%, and most preferably from about 0.03 to about 0.05% by weight. Additionally, the lytic reagent also contains a differential effective amount of a natural detergent, such as saponin, preferably at a concentration from about 0.05 to about 0.15%, most preferably from about 0.07 to about 0.09% by weight. The lytic reagent has a pH of about 1.8 to about 4.0, preferably from about 1.9 to about 3.8 and most preferably from about 2.5 to about 3.5, and an osmolality of about 5 to about 50 milliosmoles per kilogram, preferably from about 10 to about 25 milliosmoles per kilogram.

Alternatively, the lytic reagent may comprise an aqueous solution of 1-butanesulfonic acid, sodium salt, preferably at a concentration of about 0.1 to about 0.5%, and most preferably at a concentration of about 0.15 to about 0.25% by weight. Additionally, the lytic reagent also contains a differential effective amount of a natural detergent, such as saponin, preferably at a concentration from about 0.06 to about 0.2%, most preferably from about 0.1 to about 0.15% by weight. The lytic reagent has a pH of about 5.0 to about 6.0, and preferably from about 5.2 to about 5.5; and an osmolality of about 10 to about 150 milliosmoles per kilogram, preferably from about 15 to about 100 milliosmoles per kilogram.

A second, balancing solution, called a quenching reagent, is also required for white cell differential analysis, to increase the osmolality to near isotonic (about 285 to about 325 milliosmoles per kilogram), to raise the conductivity to a range acceptable to the analyzer measurement sensor requirements, and to increase the pH to near neutral for final measurement. This process is frequently flawed by insufficient separation of the white cell subpopulations, especially with respect to merging of the granulocyte, monocyte and lymphocyte populations into a continuum of signal that is difficult to separate into distinct cell subtypes. Additionally, adequate quenching of the lytic reaction is required to reduce cellular debris and resulting conductivity noise in the scattergram, to prevent such noise from unduly influencing the mathematical calculations by reducing the number of statistically valid events counted in the measurement cycle.

In the present invention, it is believed that the rate at which the acid ($H^+$) ion is released into the lysing reaction is a critical factor in separating the cell subpopulations into distinct clusters for accurate measurement. Use of the weak detergent saponin in low osmolality solution is retained as a design feature to aid in the dispersion of the red blood cell and platelet membranes and membrane remnants. The acid source may be an inorganic acid anhydride that generates the half salt of a strong acid in solution, thus providing acid ions only upon hydrolysis. Alternatively, a weak organic acid with $pK_a > 3.8$ may be used, together with a small amount of mineral such as hydrochloric acid, to adjust the reagent pH to about 3.0. This reagent also releases acid ions slowly into solution: after the mineral acid $H^+$ ion has been consumed, the dissociation equilibrium of the weak organic acid responds by releasing additional acid, repeating the equilibrium process until the reaction does not require any further acid ions. Weak organic acids are noted for their slow equilibrium kinetics, and subsequent slow release of acid ions.

Example II shows one possible composition of the weak lytic reagent and the quenching reagent, and is illustrative of a composition of matter to practice this invention.

Example II

The 5-population lysing agent of this invention was prepared from standard National Formulary, United States Pharmacopoeia or American Chemical Society grade chemicals. A lysing solution containing 0.085% (w/v) of saponin and 0.04% (w/v) of potassium pyrosulfate was prepared in deionized water, and filtered through a 0.2 micron filter to remove all particulates. The pH of this solution was about 2.9. A 27 μL sample of whole blood was added to 1,072 μL of lytic reagent and gently mixed for about 5 seconds at ambient room temperature (~23° C.). After this lysing time, 196 μL of a quenching reagent, containing 6.4% (w/v) of sodium sulfate and 0.16% (w/v) of N-(2-Hydroxyethyl)-piperazine-N'-ethanesulfonic acid, sodium salt ("sodium HEPES") in deionized water was added. The pH of this quenching reagent was about 9.75. The lysing and quenching reagents are chemically balanced to yield a final prepared blood sample with a pH of about 6.5 to 7.2, an osmolality of about 300 to 335 mos/kg, and a conductivity of about 18.8 to 19.8 mS/cm. After an additional 5 to 10 seconds, the sample was aspirated into a flow cytometry flow cell equipped for differential white blood cell analysis with a helium/neon or LED laser light source and silicon diode detectors for measuring scattered light at one or more angles to the incident beam, a radio frequency ocillator and fluid cavity for measuring cellular conductivity, and an electrical impedance volume sensor set to record data from the flow cell aperture. The three measurement sensors are respectively designed to record pulses generated by interaction of each blood cell passing through the sensing zone and plot said pulses along mathematical axes orthogonal to pulses from the d.c. impedance volume sensor. When impedance volume data are plotted against light scatter data, four distinct subpopulations are identified and quantitated. A fifth subpopulation (basophils) may be determined by plotting impedance volume data versus opacity (conductivity data divided by the d.c. volume). The scattergrams generated from the sample are shown as FIGS. 2A and B. Comparable results from the Coulter reagent system are shown as FIGS. 3A and B. The current invention provides a much more well-delineated scattergram, containing separate subpopulations for each subtype of white blood cell.

Example III

Figure 4A:
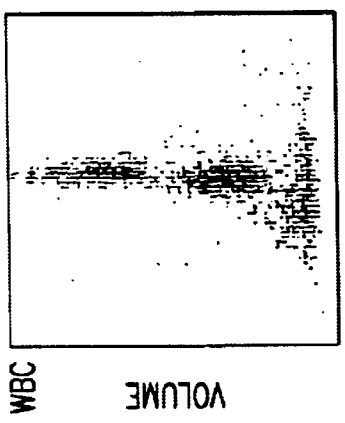
FIG. 4A is a scattergram of Example III, volume v. light scatter, using a low acidity lysing reagent.
Figure 4B:
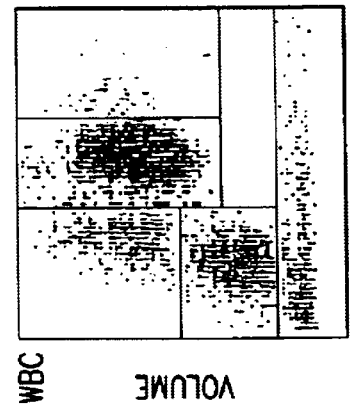
FIG. 4B is a scattergram of Example III, volume v. opacity scatter, using a low acidity lysing reagent.

The lysing reagent similar to that from Example II is modified by deleting the potassium pyrosulfate and substituting 2.0 g/L 1-butanesulfonic acid, sodium salt, and by increasing the saponin concentration to about 1.2 g/L, giving a lysing solution with a pH of about 5.2 to 5.35. The quenching reagent was prepared with a chemically balanced amount of 0.8 g/L of HEPES sodium salt, in order to yield a final blood sample solution having a pH of about 6.5 to 7.5, an osmolality of about 300 to 335 mos/kg and a conductivity of about 18.8 to 19.8 mS/cm. As in the previous example, a 27 μL sample of whole blood was added to 1,072 μL of lytic reagent and gently mixed for about 5 seconds at ambient room temperature (~23° C.), then 196 μL of the modified quenching reagent was added and mixed gently for about 10 seconds more. The sample was then subjected to analysis as in Example II. The data are plotted and displayed as described in Example II. These results are very similar to those shown in FIG. 2 and indicate that the strong acid component of the lysing reagent is not required for complete lysis and separation of the leukocyte subpopulations. These results are shown as FIGS. 4A and B.

Example IV

Figure 5A:
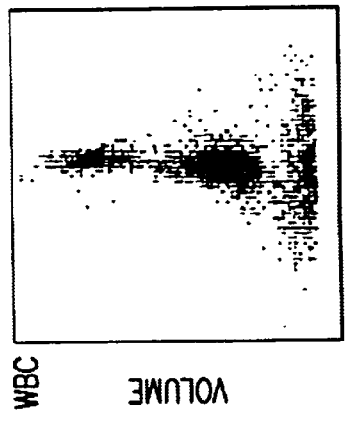
FIG. 5A is a scattergram of Example IV, volume v. light scatter, using glutaric acid lyse.
Figure 5B:
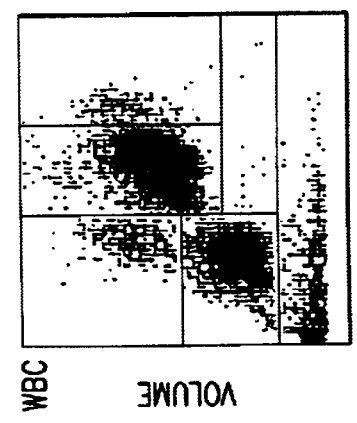
FIG. 5B is a scattergram of Example IV, volume v. opacity scatter, using glutaric acid lyse.

Another lysing reagent containing 0.085% (w/v) saponin and 0.05% (w/v) of glutaric acid was acidified with 0.009% hydrochloric acid to give a pH of about 3.2, then diluted to volume with deionized water and filtered through a 0.2 micron filter. The quenching solution of example II was used without modification. A 27 μL sample of whole blood was added to 1,072 μL of this lytic reagent and gently mixed for about 5 seconds at ambient room temperature (~23° C.), then 196 μL of quenching reagent from Example II was added and mixed gently for about 10 seconds. The sample was then subjected to analysis as in Example II, and the data were plotted and displayed. These results were very similar to those of previous examples II and III. They are shown as FIGS. 5A and B. Significantly lower amounts of available acid gave the same analytical results as Example II, with only moderately more debris pulses in the lowest box of the scattergram.

Acidification of a solution of a weak organic acid with strong mineral acid, such as hydrochloric acid, results in the suppression of ionization of the proton associated with the organic acid. Requirements for acid by the lytic reaction are supplied by consumption of the free hydrogen ions in solution, followed by a relatively slow disassociation of the suppressed organic acid to supply additional hydrogen ion for completion of the lysis and separation of the leukocyte subpopulations.

In practice, these examples demonstrate that substantial amounts of acid are not required to enhance the lytic reaction, as claimed in U.S. Pat. No. 5,731,206 (Ledis, et al.) and others. Even salts of weak organic acids can hydrolyze at a very slow rate in solutions of higher pH, giving rise to limited and therefore regulated amounts of acidity, sufficient to enhance the lysing action of the saponin component, while avoiding damage to the leukocyte components by larger amounts of strong acid. Significant control of the delivery of hydrogen ions into the sample lysing solution is apparently the most important requirement of this reaction, in order to produce significantly undamaged white blood cell subpopulations for efficient and accurate differentiation and quantification.

This combination of reagent formulations unexpectedly provides scattergrams of the white blood cell subpopulations for each cell subtype, well delineated and confined to the individual subtype data ranges calibrated into the analyzer software.

An unexpected benefit of the use of these reagents of the present invention, in addition to the improved precision of results afforded by cleaner separation of the cell subtype populations, was that the analyzer's flagging algorithms are not triggered as often, especially as "high level" flags that require operator intervention or further testing by manual methods in order to resolve potentially erroneous data that might result in mis-diagnosis or mis-treatment of a patient. The analyzer equipped with the reagents of this invention generally reported no error flags or only "low level" error flags, and therefore less serious instrument errors. Low level instrument error flags do not usually require resolution by independent methods. These follow-up methods are time-consuming and therefore expensive to perform, often delaying the timely reporting of laboratory results to the physician.

The advantages of these new reagents and the methods of using them are most apparent in the analyses of abnormal and aged blood specimens, in which the current Coulter reagent system usually displays poor separation and inaccurate enumeration of white blood cell subpopulations, in addition to "higher" levels of error flagging.

Although the invention has been described in terms of preferred embodiments, nevertheless changes and modifications will be evident to those skilled in the art. Such changes and modifications are deemed to come within the purview of the invention as claimed.

What is claimed is:

1. A multi-purpose isotonic diluent reagent consisting of an aqueous solution of from about 1.5 to about 1.8% w/v of a single alkali metal sulfate salt selected from the class consisting of sodium sulfate, potassium sulfate and the mixture of sodium sulfate and potassium sulfate which dissociates into individual ions for establishing isotonicity, osmolality and conductivity of the reagent, and additives of a buffering agent, a chelating agent, an anesthetic agent, and a germicidal agent, the diluent having a pH of 7.0 to 7.2, and osmolality of 285 to 335 milliosmoles/kg and a conductivity 18 to 20 milliSiemens/cm.

2. A multi-purpose isotonic diluent reagent according to claim 1 wherein the anesthetic agent is procaine hydrochloride.

3. A multi-purpose isotonic diluent reagent according to claim 1 wherein the single alkali metal salt consists of an aqueous solution of sodium sulfate.

* * * * *